(12) United States Patent
Hong et al.

(10) Patent No.: US 8,766,974 B2
(45) Date of Patent: Jul. 1, 2014

(54) DISPLAY APPARATUS AND METHOD

(75) Inventors: Ji Young Hong, Seongnam-si (KR); Dong Kyung Nam, Yongin-si (KR); Seo Young Choi, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 412 days.

(21) Appl. No.: 13/137,123

(22) Filed: Jul. 21, 2011

(65) Prior Publication Data

US 2012/0098823 A1 Apr. 26, 2012

(30) Foreign Application Priority Data

Oct. 22, 2010 (KR) ........................ 10-2010-0103374

(51) Int. Cl.
*G06T 15/00* (2011.01)
*G06F 19/00* (2011.01)

(52) U.S. Cl.
CPC ............ *G06F 19/321* (2013.01); *G06F 19/345* (2013.01)
USPC ............. 345/419; 345/418; 348/42; 351/209; 351/246; 382/154

(58) Field of Classification Search
CPC .................................................... G06F 19/345
USPC ........... 345/418, 419; 351/209, 246; 382/154; 348/42

See application file for complete search history.

(56) References Cited

U.S. PATENT DOCUMENTS

| | | | |
|---|---|---|---|
| 6,996,267 B2 * | 2/2006 | Tabata | 382/154 |
| 7,344,251 B2 * | 3/2008 | Marshall | 351/246 |
| 7,438,418 B2 * | 10/2008 | Marshall | 351/246 |
| 7,815,311 B2 * | 10/2010 | Johns et al. | 351/209 |
| 7,880,621 B2 * | 2/2011 | Kalik | 340/573.1 |
| 8,038,614 B2 * | 10/2011 | Gobeyn et al. | 600/300 |
| 8,390,674 B2 * | 3/2013 | Kim et al. | 348/42 |

FOREIGN PATENT DOCUMENTS

| | | |
|---|---|---|
| JP | 2002-223458 | 8/2002 |
| JP | 2007-20130 | 1/2007 |
| JP | 2008-257431 | 10/2008 |
| KR | 10-2009-0037373 | 4/2009 |
| KR | 10-2009-0102705 | 9/2009 |

* cited by examiner

*Primary Examiner* — Phu K Nguyen
(74) *Attorney, Agent, or Firm* — Staas & Halsey LLP

(57) ABSTRACT

Provided is a display apparatus that may estimate a degree of visual fatigue corresponding to an input 3-dimensional (3D) image, using a visual fatigue model to estimate the degree of visual fatigue of a user. The display apparatus may reduce the degree of visual fatigue of the user by rescaling a depth level of the input 3D image based on the degree of visual fatigue.

18 Claims, 6 Drawing Sheets

DISPLAY APPARATUS AND METHOD

CROSS-REFERENCE TO RELATED APPLICATIONS

This application claims the priority benefit of Korean Patent Application No. 10-2010-0103374, filed on Oct. 22, 2010, in the Korean Intellectual Property Office, the disclosure of which is incorporated herein by reference.

BACKGROUND

1. Field

One or more example embodiments of the present disclosure relate to a general-purpose display apparatus for providing a 3-dimensional (3D) image, and more particularly, to a 3D display apparatus and a method for providing different images, each having a disparity between the left eye and the right eye of a human using a stereoscopic image or a multi-view image.

2. Description of the Related Art

A 3-dimensional (3D) image display apparatus refers to an image display apparatus that may provide different images reflecting a disparity between the left eye and right eye of a human in order to provide a 3D effect.

A 3D image display apparatus may include a stereoscopic type providing a left eye viewpoint image and a right eye viewpoint image, and a multi-view image providing an image from various viewpoints.

When configuring a 3D display, visual fatigue due to a convergence-accommodation (C-A) difference may occur.

In the past, in order to resolve the visual fatigue, schemes of collectively down scaling a depth level of an input 3D image without estimating a degree of visual fatigue, regenerating a 3D image based on several simple assumptions, and the like have been disclosed.

However, when following the aforementioned suggestions, dynamically regenerating an input 3D image by adaptively estimating visual fatigue, which may result in considerable 3D image distortion compared with the improvement in the visual fatigue, may be difficult.

SUMMARY

The foregoing and/or other aspects are achieved by providing a display apparatus including a processor to control one or more processor-executable units, a visual fatigue estimating unit to estimate a degree of visual fatigue corresponding to an input 3-dimensional (3D) image, and an image adjusting unit to rescale a depth level of the input 3D image based on the degree of visual fatigue.

The visual fatigue estimating unit may include a motion vector calculating unit to calculate a motion vector corresponding to the input 3D image, and a visual fatigue determining unit to calculate the degree of visual fatigue using the calculated motion vector.

The visual fatigue estimating unit may include a depth profile calculating unit to calculate a depth profile corresponding to the input 3D image, and a visual fatigue determining unit to calculate the degree of visual fatigue using the calculated depth profile.

The visual fatigue estimating unit may calculate the degree of visual fatigue using a visual fatigue model associated with at least one of the motion vector corresponding to the input 3D image, and the depth profile corresponding to the input 3D image.

The visual fatigue estimating unit may include a lookup table database to store a lookup table associated with the visual fatigue model.

The image adjusting unit may include an optimal depth profile calculating unit to calculate an optimal depth profile to reduce the degree of visual fatigue, and a depth level rescaling unit to rescale a depth level of the input 3D image using the calculated optimal depth profile.

The visual fatigue estimating unit may estimate the degree of visual fatigue based on convergence-accommodation (C-A) difference using at least one of a viewing distance between the display apparatus and a user, and a distance between the left eye and the right eye of the user.

The foregoing and/or other aspects are achieved by providing a display method including estimating a degree of visual fatigue corresponding to an input 3D image, and rescaling, by way of a processor, a depth level of the input 3D image based on the degree of visual fatigue.

The estimating of the degree of visual fatigue may include calculating a motion vector corresponding to the input 3D image, and calculating the degree of visual fatigue using the calculated motion vector.

The estimating of the degree of visual fatigue may include calculating a depth profile corresponding to the input 3D image, and calculating the degree of visual fatigue using the calculated depth profile.

The estimating of the degree of visual fatigue may calculate the degree of visual fatigue using a visual fatigue model associated with at least one of the motion vector corresponding to the input 3D image, and the depth profile corresponding to the input 3D image.

The estimating of the degree of visual fatigue may calculate the degree of visual fatigue using a lookup table associated with the visual fatigue model.

The foregoing and/or other aspects are achieved by providing a display apparatus including a processor to control one or more processor-executable units, a visual fatigue estimating unit to identify a characteristic of a 3-dimensional (3D) image and to estimate a degree of visual fatigue that a user may experience while viewing the 3D image based on the identified characteristic, and an image adjusting unit to provide an image in which visual fatigue has been reduced, corresponding to the 3D image, based on the degree of visual fatigue estimated by the visual fatigue estimating unit.

Additional aspects of embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of embodiments, taken in conjunction with the accompanying drawings of which.

DETAILED DESCRIPTION

Reference will now be made in detail to embodiments, examples of which are illustrated in the accompanying drawings, wherein like reference numerals refer to like elements throughout. Embodiments are described below to explain the present disclosure by referring to the figures.

Figure 1:
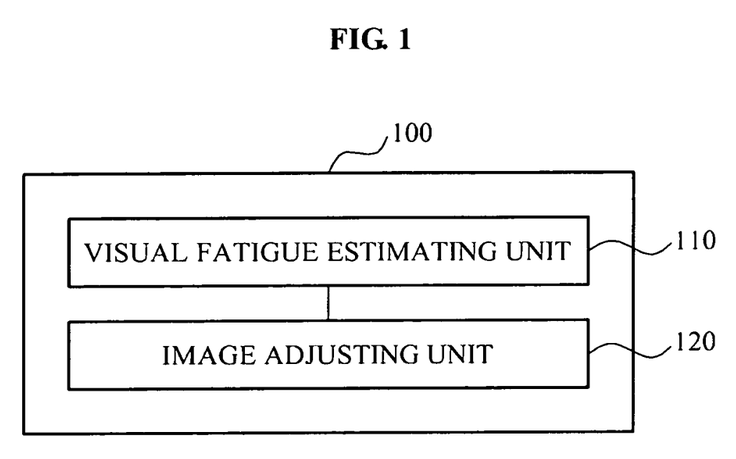
FIG. 1 illustrates a display apparatus according to example embodiments.

FIG. 1 illustrates a display apparatus 100 according to example embodiments.

A visual fatigue estimating unit 110 of the display apparatus 100 may identify a characteristic of a 3-dimensional (3D) image to be input, and estimate a degree of visual fatigue that a user may experience when viewing the 3D image.

When a 3D image is displayed, a different image may be provided to the left eye and the right eye of the user. Thus, the user may experience visual fatigue due to a convergence-accommodation (C-A) difference between the left eye and the right eye of the user.

As is well known, when a distance from an object viewed by the user is changed, a human eye may focus a created image on the retina by adjusting the thickness of the lens, in response to the change.

Here, both eyes may project an image, to the center of the left eye and the right eye, from an identical object through an eye movement of convergence and accommodation depending on the viewing distance from the object, and thus humans may feel a 3D effect.

When an object from the real environment is observed, a depth in which convergence occurs and a depth in which accommodation occurs may be identical, and accordingly visual fatigue may not occur.

However, as described above, the accommodation may need to correspond to a depth of a screen on which an image is displayed, that is, a viewing distance, by providing, to the left eye and the right eye of a human, an artificially generated left viewpoint image and an artificially generated right viewpoint image. An extent of the convergence of both eyes may need to correspond to a depth different from the depth of the screen on which the image is displayed based on a disparity between the two eyes, that is, a virtual position based on a depth of an object. Here, a difference between convergence and accommodation may occur and accordingly, visual fatigue may occur.

According to example embodiments, a degree of visual fatigue that a user may experience when viewing a 3D image may be estimated. The degree of visual fatigue may be estimated using a visual fatigue model based on characteristics of a 3D image to be input.

For example, visual fatigue may be great when a disparity between images from each viewpoint that may be provided to the left eye and the right eye of the user is great, that is, a difference in depth level is great.

Also, visual fatigue may be great when significant movement of an object in a scene from a different frame occurs. That is, the visual fatigue may be greater when the user views a 3D image of a dynamic scene than a 3D image of a static scene.

Therefore, the visual fatigue estimating unit 110 may analyze a depth level profile of the input 3D image, or calculate a motion vector between frames, or both, and thereby estimate how much visual fatigue the user may experience when viewing the input 3D image.

A process of estimating a degree of visual fatigue with respect to an input 3D image, performed for example by the visual fatigue estimating unit 110, will be further described with reference to FIGS. 2 through 5.

An image adjusting unit 120 of the display apparatus 100 may provide an image where visual fatigue is reduced by adjusting the input 3D image or by regenerating the input 3D image.

The image adjusting unit 120 may calculate an optimal depth profile to reduce the degree of visual fatigue, and rescale a depth level of the input 3D image using the calculated depth profile.

A process of reducing visual fatigue by adjusting the input 3D image, performed for example by the image adjusting unit 120, will be further described with reference to FIGS. 3 through 5.

Figure 2:
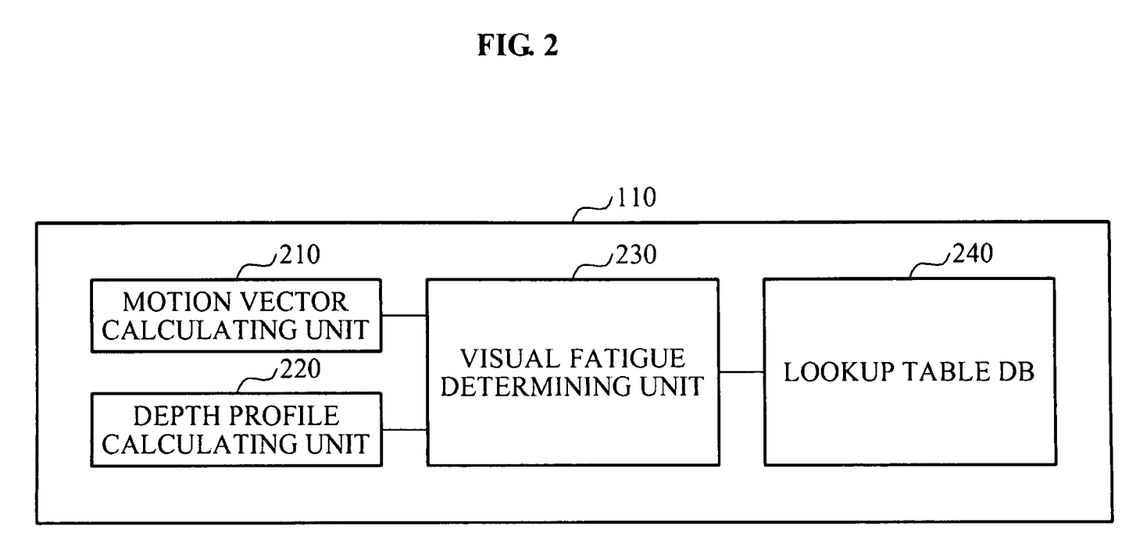
FIG. 2 illustrates a configuration of a visual fatigue estimating unit of the display apparatus of FIG. 1.

FIG. 2 illustrates a configuration of the visual fatigue estimating unit 110 of the display apparatus 100 of FIG. 1.

When viewing a still 3D image, an eye movement having a predetermined convergence angle may be performed once. In contrast, when viewing an object moving in a depth direction using a 3D image, convergence and accommodation may be continuously performed.

A convergence angle of an object and a convergence angle of a human eye may not be exactly identical, and the difference between the convergences may become greater as speed in a depth direction increases. Accordingly, if the main factor causing visual fatigue corresponds to a C-A difference, the degree of visual fatigue may increase when viewing a video having dynamic motion in comparison to viewing a static 3D image.

As to the visual fatigue due to the dynamic movement, when directionality of the movement becomes greater and a speed of the movement increases, the C-A difference may become greater and consequently, the visual fatigue may increase.

The visual fatigue estimating unit 110 may estimate the degree of visual fatigue using a viewing distance of a viewer, a distance between the left eye and the right eye, a motion vector (MV) between frames of an input 3D image, and depth profile information.

Here, a motion vector calculating unit 210 may estimate a motion of a 3D image to be input, and may calculate an MV value that may represent the input 3D image.

The MV value may be calculated using a motion vector calculation method and the like that is typically used to encode a two-dimensional (2D) image or to compress the 2D image.

Figure 4:
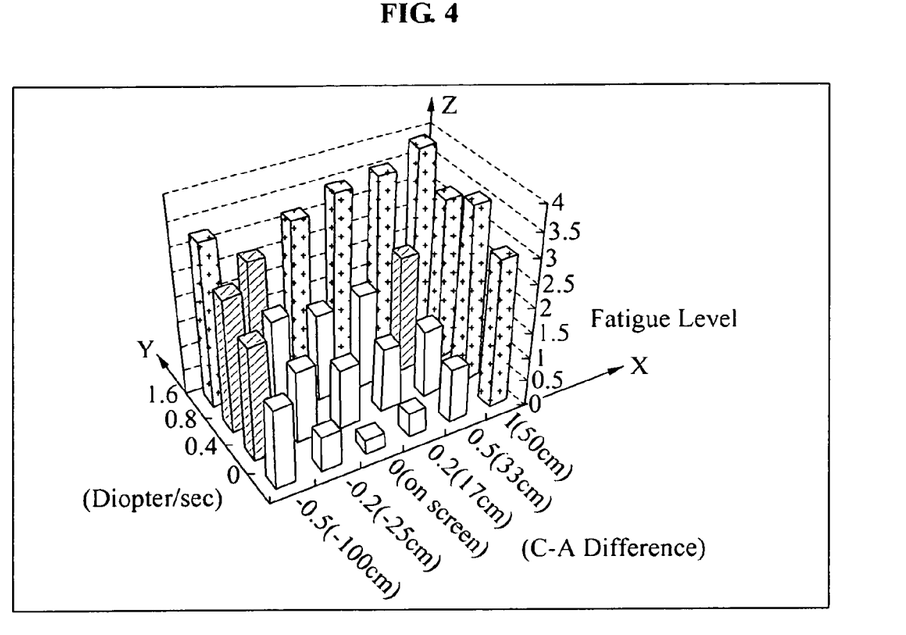
FIG. 4 illustrates a visual fatigue model that may used by a visual fatigue estimating unit according to example embodiments.
Figure 5:
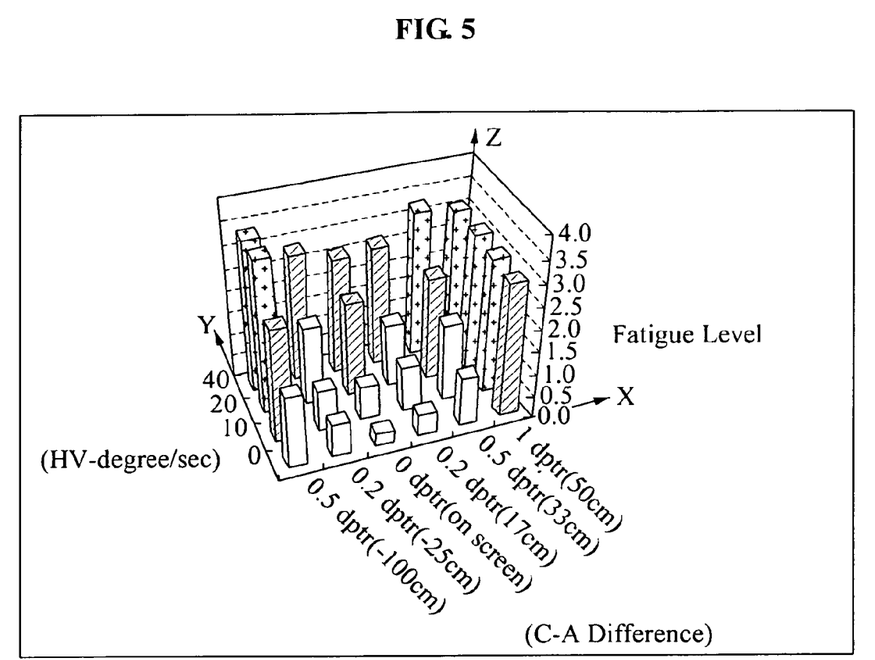
FIG. 5 illustrates a visual fatigue model that may used by a visual fatigue estimating unit according to example embodiments.

As illustrated in FIG. 4 and FIG. 5, a degree of visual fatigue may be different based on a type of motion of an input 3D image. Accordingly, a different visual fatigue model may use at least one of a different lookup table (LUT) and a different function.

Hereinafter, a motion characteristic of an image having a slight amount of change in a depth of a scene, and having a great movement in a planar direction will be referred to as a "planar motion." A motion having a great amount of change in the depth will be referred to as a "depth motion."

The motion vector calculating unit 210 may calculate an MV corresponding to a value of a direction and a value of a size with respect to a motion image.

In case of a video, when comparing a previous frame and a current frame, a background may remain the same and only a partial object may move in many cases. Accordingly, the motion vector calculating unit 210 may calculate the MV using n frames, for example, frame t, frame t−1, and the like).

A depth profile calculating unit 220 may perform a function to calculate a representative depth value by calculating a depth profile corresponding to a characteristic of a depth level of an input 3D image.

A viewing distance, a distance between a user and a 3D object, or a distance between a screen and a 3D object may be used to calculate a depth of an input 3D image.

According to example embodiments, the viewing distance may be calculated using information input by a user viewing distance calculating apparatus (not shown), or by directly inputting a viewing distance.

The depth profile calculating unit 220 may calculate a representative depth value at a corresponding frame of an input 3D image, and the representative depth value may be calculated using a frequency of an average value, or a frequency of a depth value, an accumulation, and the like.

A depth profile such as the calculated representative depth and the like, and/or the motion vector calculated by the motion vector calculating unit 210 may be transmitted to a visual fatigue determining unit 230.

The visual fatigue determining unit 230 may determine a degree of visual fatigue with respect to an input 3D image using a visual fatigue model configured or determined in advance.

A process of determining, by the visual fatigue determining unit 230, the degree of visual fatigue by applying the depth profile or the motion vector to the visual fatigue model, or both, may be performed using a lookup table stored in a lookup table database 240, and/or using a visual fatigue function.

An example of the visual fatigue function corresponds to a graph as illustrated in FIG. 4 and FIG. 5. However, the visual fatigue model should not be construed as limited to the example embodiments, and various modifications and variations can be made without departing from the spirit or the scope of the disclosure.

The visual fatigue model may be configured in advance by an experiment where an MV of an input image and a depth profile is a factor or variable.

That is, images, each having a different depth profile and/or a different MV may be shown to a subject, and then visual fatigue experienced by the subject may be estimated. A visual fatigue model may be estimated by obtaining statistical data by estimating the visual fatigue from a plurality of subjects.

FIG. 4 and FIG. 5 each correspond to an example of calculating a visual fatigue model with respect to a depth motion and a planar motion.

In FIG. 4, the X-axis indicates an extent of a C-A difference of a 3D image, and the Y-axis indicates an amount of change in a depth direction motion. The Z-axis indicates visual fatigue, which may be selected as a value from 0 to 4 in the example embodiments. A relatively large value of the Z-axis may indicate a higher visual fatigue while a relatively small value of the Z-axis may indicate a lower visual fatigue.

In FIG. 5, the X-axis indicates an extent of a C-A difference of a 3D image, and the Y-axis indicates an amount of change in a planar direction motion. The Z-axis indicates visual fatigue.

Referring back to FIG. 2, the visual fatigue determining unit 230 may determine a degree of visual fatigue corresponding to an input 3D image using a lookup table (LUT) configured by numerically expressing the visual fatigue models of FIG. 4, FIG. 5, or the like. Here, the LUT may be stored in the lookup table database 240, and may be used by the visual fatigue determining unit 230.

The visual fatigue determining unit 230 may also determine the degree of visual fatigue using a calculating function with respect to a degree of visual fatigue configured by approximating the visual fatigue model.

The calculating function with respect to the degree of visual fatigue may be designed based on a psychophysical experiment as described above, and may be expressed by the following equations.

$$DVF=1.937*speed-4.375*depth-0.297*(speed*depth)-0.158*(speed^2)+2.124*(depth^2)+2.932 \quad \text{[Equation 1]}$$

Equation 1 corresponds to a modeling function design based on a depth motion.

A model design based on a planar motion may be expressed by Equation 2.

$$DVF=1.916*speed-5.268*depth-0.530*(speed*depth)-0.190*(speed^2)+2.461*(depth^2)+3.372 \quad \text{[Equation 2]}$$

The functions of Equation 1 and Equation 2 that may calculate a degree of visual fatigue (DVF) may correspond to an approximate expression considering up to a quadratic term.

In Equation 1 and Equation 2, a variable 'speed' indicates a speed of a motion, and a variation 'depth' indicates a C-A difference.

Referring back to FIG. 4 and FIG. 5, when a speed is fast and a depth is great, that is, when the difference between a calculated MV value and a calculated depth value, between a previous frame and a current frame of an input image, is great, the degree of visual fatigue tends to be great.

In addition to the depth motion or the planar motion, each function may be either identical or different depending on directionality of motion.

For example, when there are multiple movements to a depth direction in an input image, the above expressed equations may be used to infer the degree of visual fatigue.

However, when there are multiple movements, which are neither in the depth direction nor in the planar direction, but rather in other directions, for example, a predetermined direction such as a vertical direction, a horizontal direction, a diagonal direction, and the like, a function with respect to the degree of fatigue may be differently expressed by various equations. Furthermore, variations can be made without departing from the scope of the disclosure.

According to example embodiments, the degree of fatigue may be inferred with respect to both the depth motion and the planar motion in an input 3D image, and then a depth of the 3D image may be adjusted based on motion of a direction in which a greater degree of visual fatigue occurs.

In the case of the depth motion, while the user observes the depth motion, a varying amount of difference between convergence and accommodation may occur, whereas in the case of the planar motion, an identical amount of difference between convergence and accommodation may occur. Both the depth motion and the planar motion may correspond to the C-A difference, however, both the depth motion and the planar motion may be different factors causing fatigue, and may be processed separately.

The image adjusting unit 120 of the display apparatus 100 may perform a function to control the degree of fatigue using the visual fatigue model since a depth profile where the degree of fatigue decreases may be inversely estimated using the degree of visual fatigue calculated by the above equation.

An operation of the image adjusting unit 120 will be further described with reference to FIG. 3.

Figure 3:
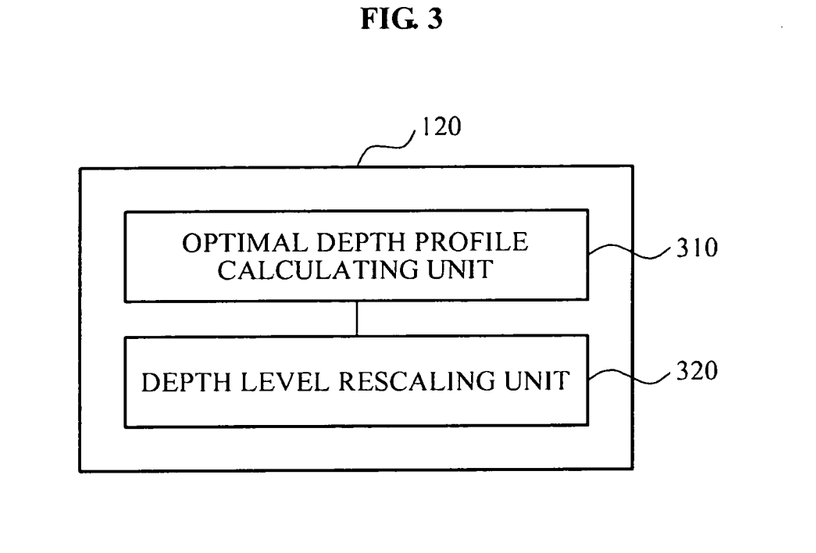
FIG. 3 illustrates a configuration of an image adjusting unit of the display apparatus of FIG. 1.

FIG. 3 illustrates a configuration of the image adjusting unit 120 of the display apparatus 100 of FIG. 1.

An optimal depth profile calculating unit 310 may respond to a degree of visual fatigue of a current frame of an input 3D image estimated by the visual fatigue estimating unit 110, and may calculate an optimal depth profile using a LUT or a function that optimally maps the degree of fatigue of the input 3D image.

The optimal depth profile may correspond to a characteristic of the input 3D image, and may include a depth level and the like to reduce visual fatigue without distortion.

The optimal depth profile may be provided to a depth level rescaling unit 320, and the depth level rescaling unit 320 may rescale a depth level of the input 3D image.

According to the above example embodiments, a depth level rescale may be globally performed with respect to an entire input 3D image of a single frame. However, an adaptive depth level rescale with respect to a portion of the input 3D image may also be possible.

By the above-described process, quality degradation of an input 3D image may be prevented, and visual fatigue may be significantly reduced.

Figure 6:
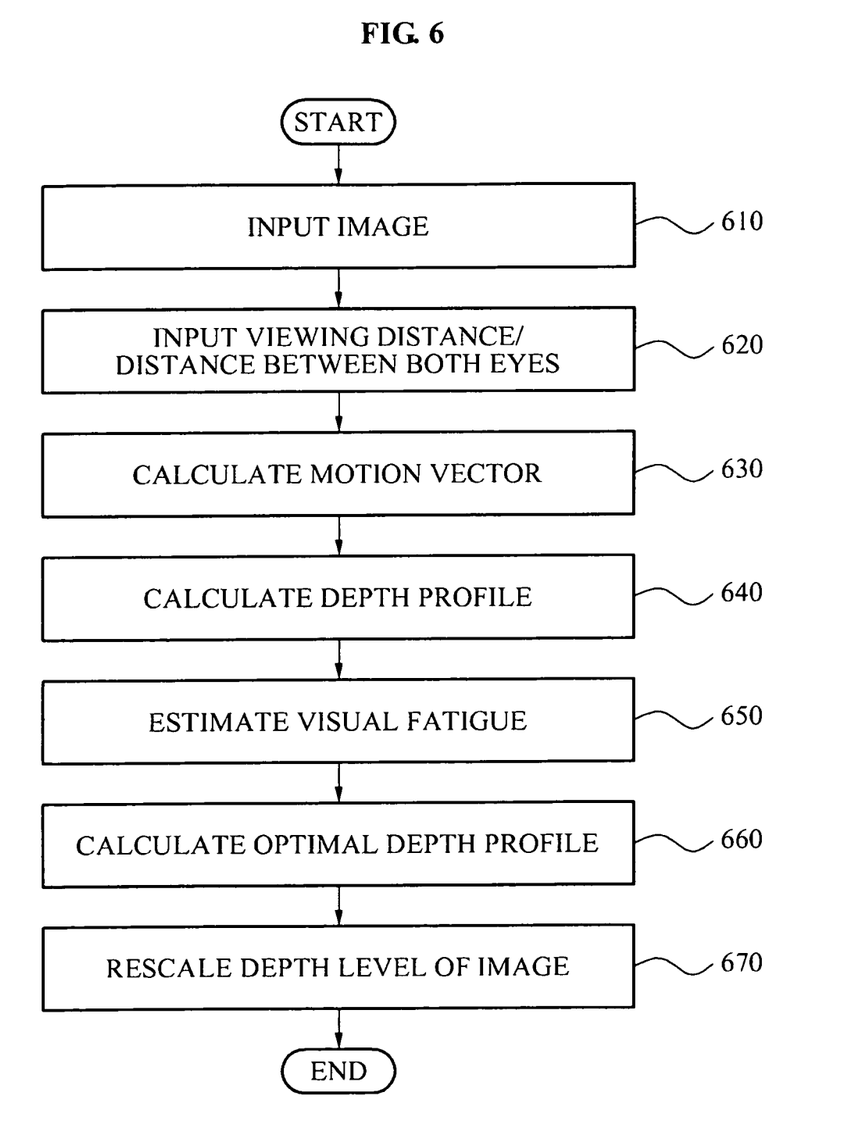
FIG. 6 illustrates a display method according to example embodiments.

FIG. 6 illustrates a display method according to example embodiments.

In operation 610, a 3D image may be input.

In operation 620, a viewing distance from which a user may view the 3D image using a display apparatus, and/or a distance between the left eye and the right eye of the user may be input. The viewing distance and/or the distance between the both eyes may be used to determine a C-A difference.

In operation 630, the motion vector calculating unit 210 of the display apparatus 100 may calculate a motion vector corresponding to the input 3D image. The result of the motion vector calculation may be represented as a representative MV as described above.

In operation 640, the depth profile calculating unit 220 of the display apparatus 100 may calculate a depth profile.

In operation 650, the visual fatigue determining unit 230 may estimate visual fatigue corresponding to the input 3D image, using the visual fatigue model as described with reference to FIG. 4 and FIG. 5.

In operation 660, the optimal depth profile calculating unit 310 of the display apparatus 100 may calculate an optimal depth profile to reduce the visual fatigue on the condition that quality degradation of an image or visual distortion of the image is improved.

In operation 670, the depth level rescaling unit 320 may rescale a depth level of the input 3D image, and adjust to a 3D image with reduced visual fatigue.

The above processes described with reference to FIG. 6 may correspond to corresponding processes as described with reference to FIGS. 1 through 5.

The method according to the above-described embodiments may be recorded in non-transitory, computer-readable media including program instructions to implement various operations embodied by a computer. The media may also include, alone or in combination with the program instructions, data files, data structures, and the like. Examples of non-transitory, computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like.

Examples of program instructions include both machine code, such as produced by a compiler, and files containing higher level code that may be executed by the computer using an interpreter. The described hardware devices may be configured to act as one or more software modules in order to perform the operations of the above-described embodiments, or vice versa. Any one or more of the software modules or units described herein may be executed by a dedicated processor unique to that unit or by a processor common to one or more of the modules. The described methods may be executed on a general purpose computer or processor or may be executed on a particular machine such as the display apparatuses described herein.

Although embodiments have been shown and described, it would be appreciated by those skilled in the art that changes may be made in these embodiments without departing from the principles and spirit of the disclosure, the scope of which is defined by the claims and their equivalents.

What is claimed is:

1. A display apparatus, comprising:
a processor to control one or more processor-executable units;
a visual fatigue estimating unit to estimate a degree of visual fatigue corresponding to an input 3-dimensional (3D) image, wherein the visual fatigue estimating unit comprises:
a motion vector calculating unit to calculate a motion vector corresponding to the input 3D image; and
a visual fatigue determining unit to estimate the degree of visual fatigue using the motion vector calculated by the motion vector calculating unit; and
an image adjusting unit to rescale a depth level of the input 3D image based on the degree of visual fatigue.

2. The display apparatus of claim 1, wherein the visual fatigue estimating unit further comprises:
a depth profile calculating unit to calculate a depth profile corresponding to the input 3D image; and
wherein the visual fatigue determining unit further estimates the degree of visual fatigue using the depth profile calculated by the depth profile calculating unit.

3. The display apparatus of claim 2, wherein the visual fatigue estimating unit calculates the degree of visual fatigue using a visual fatigue model associated with the motion vector corresponding to the input 3D image calculated by the motion vector calculating unit, and the depth profile corresponding to the input 3D image calculated by the depth profile calculating unit.

4. The display apparatus of claim 3, wherein the visual fatigue estimating unit comprises a lookup table database to store a lookup table associated with the visual fatigue model.

5. The display apparatus of claim 1, wherein the image adjusting unit comprises:
an optimal depth profile calculating unit to calculate an optimal depth profile to reduce the degree of visual fatigue; and
a depth level rescaling unit to rescale a depth level of the input 3D image using the optimal depth profile calculated by the optimal depth profile calculating unit.

6. The display apparatus of claim 1, wherein the visual fatigue estimating unit estimates the degree of visual fatigue based on a convergence-accommodation difference using at least one of a viewing distance between the display apparatus and a user, and a distance between a left eye and a right eye of the user.

7. A display method, comprising:
estimating a degree of visual fatigue corresponding to an input 3-dimensional (3D) image, wherein the estimating of the degree of visual fatigue comprises:
calculating a motion vector corresponding to the input 3D image; and calculating the degree of visual fatigue using the calculated motion vector; and rescaling, by way of a processor, a depth level of the input 3D image based on the degree of visual fatigue.

8. The display method of claim 7, wherein the estimating of the degree of visual fatigue further comprises:

calculating a depth profile corresponding to the input 3D image; and calculating the degree of visual fatigue using the calculated depth profile and the calculated motion vector.

9. The display method of claim 8, wherein the estimating of the degree of visual fatigue includes calculating the degree of visual fatigue using a visual fatigue model associated with the motion vector corresponding to the input 3D image and the depth profile corresponding to the input 3D image.

10. The display method of claim 9, wherein the estimating of the degree of visual fatigue calculates the degree of visual fatigue using a lookup table associated with the visual fatigue model.

11. The display method of claim 7, wherein the rescaling of the depth level of the input 3D image comprises:

calculating an optimal depth profile to reduce the degree of visual fatigue; and rescaling a depth level of the input 3D image using the calculated optimal depth profile.

12. The display method of claim 7, further comprising:

receiving at least one of a viewing distance of a user, and a distance between a left eye and a right eye of the user, wherein the estimating of the degree of visual fatigue estimates the degree of visual fatigue based on a convergence-accommodation difference using at least one of the viewing distances of the user, and the distance between the left eye and the right eye of the user.

13. A non-transitory computer-readable medium comprising a program for instructing a computer to perform the method of claim 7.

14. A display apparatus comprising:

a processor to control one or more processor-executable units;

a visual fatigue estimating unit to identify a characteristic of a 3-dimensional (3D) image and to estimate a degree of visual fatigue that a user may experience while viewing the 3D image based on the identified characteristic, wherein the visual fatigue estimating unit comprises:

a motion vector calculating unit to calculate a motion vector corresponding to the input 3D image; and a visual fatigue determining unit to estimate the degree of visual fatigue using the motion vector calculated by the motion vector calculating unit; and an image adjusting unit to provide an image in which visual fatigue has been reduced, corresponding to the 3D image, based on the degree of visual fatigue estimated by the visual fatigue estimating unit.

15. The display apparatus of claim 14, wherein in the identifying of the characteristic, the visual fatigue estimating unit analyzes a depth level profile of the 3D image and calculates the motion vector between frames of the image.

16. The display apparatus of claim 14, wherein in the image adjusting unit, the image in which visual fatigue has been reduced is provided by adjusting the 3D image or by regenerating the 3D image based on the degree of visual fatigue estimated by the visual fatigue estimating unit.

17. The display apparatus of claim 16, wherein the image adjusting unit further comprises:

a depth profile calculating unit to calculate an optimal depth profile using at least one of a look-up table and a function that optimally maps the degree of fatigue of the 3D image based on the degree of visual fatigue estimated by the visual fatigue estimating unit.

18. The display apparatus of claim 17, wherein in the image adjusting unit further comprises:

a depth level rescaling unit to rescale the depth level of the input 3D image based on the optimal depth profile calculated by the depth profile calculating unit.

* * * * *